(12) United States Patent
Edberg

(10) Patent No.: US 9,404,141 B2
(45) Date of Patent: *Aug. 2, 2016

(54) METHOD FOR DETECTING THE PRESENCE OR ABSENCE OF A TARGET MICROBE IN A TEST SAMPLE

(71) Applicant: Pilots Point LLC, Sarasota, FL (US)

(72) Inventor: Stephen C. Edberg, Longboat Key, FL (US)

(73) Assignee: Pilots Point, LLC, Sarasota, FL (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/304,481

(22) Filed: Jun. 13, 2014

(65) Prior Publication Data

US 2014/0295473 A1   Oct. 2, 2014

Related U.S. Application Data

(60) Division of application No. 13/943,400, filed on Jul. 16, 2013, now Pat. No. 8,846,336, and a continuation-in-part of application No. 12/823,665, filed on Jun. 25, 2010, now Pat. No. 8,546,103.

(60) Provisional application No. 61/269,588, filed on Jun. 27, 2009.

(51) Int. Cl.
| | |
|---|---|
| *C12Q 1/04* | (2006.01) |
| *C12Q 1/06* | (2006.01) |
| *G01N 21/78* | (2006.01) |
| *C12Q 1/14* | (2006.01) |
| *C12Q 1/10* | (2006.01) |
| *C12Q 1/34* | (2006.01) |

(52) U.S. Cl.
CPC .. *C12Q 1/06* (2013.01); *C12Q 1/04* (2013.01); *C12Q 1/045* (2013.01); *C12Q 1/10* (2013.01); *C12Q 1/14* (2013.01); *C12Q 1/34* (2013.01); *G01N 21/78* (2013.01); *C12Q 2304/00* (2013.01)

(58) Field of Classification Search
CPC ...................................................... C12Q 1/045
See application file for complete search history.

(56) References Cited

U.S. PATENT DOCUMENTS

| | | | | |
|---|---|---|---|---|
| 8,268,579 B2 * | 9/2012 | Edberg | | 435/34 |
| 8,268,580 B2 * | 9/2012 | Edberg | | 435/34 |
| 8,420,347 B2 * | 4/2013 | Edberg | | 435/36 |
| 8,524,468 B2 * | 9/2013 | Edberg | | 435/34 |
| 8,546,103 B2 * | 10/2013 | Edberg | | 435/36 |
| 8,765,395 B2 * | 7/2014 | Edberg | | 435/14 |
| 8,846,336 B2 * | 9/2014 | Edberg | | 435/34 |
| 2014/0227737 A1 * | 8/2014 | Kshirsagar | | 435/34 |

* cited by examiner

Primary Examiner — Ralph Gitomer
(74) Attorney, Agent, or Firm — O'Shea Getz P.C.

(57) ABSTRACT

A method of detecting the presence or absence of a target microbe in a test sample is provided. The method includes the steps of: a) providing a test mixture that includes organic micro particles in a form that promotes the formation of a microbial biofilm, operative amounts of essential vitamins and elements needed to support growth of the target microbe, and a metabolizable substrate which can be metabolized by the target microbe t the extent needed to support continued reproductive growth thereof, and which cannot be metabolized by other viable microbes in the test sample, whereupon a sensible characteristic of the sample is altered when the substrate is metabolized; b) providing a test sample obtained from a biological, environmental, or food source, and combining the test sample in unprocessed form with the test mixture to form an admixture: and c) detecting the presence or absence of target microbes in the sample based on the presence or absence of the detectable characteristic. The micro particles are in a relative amount within the test mixture that is effective to accelerate the formation of microbial biofilms within the admixture of the test sample and the test mixture.

25 Claims, 2 Drawing Sheets

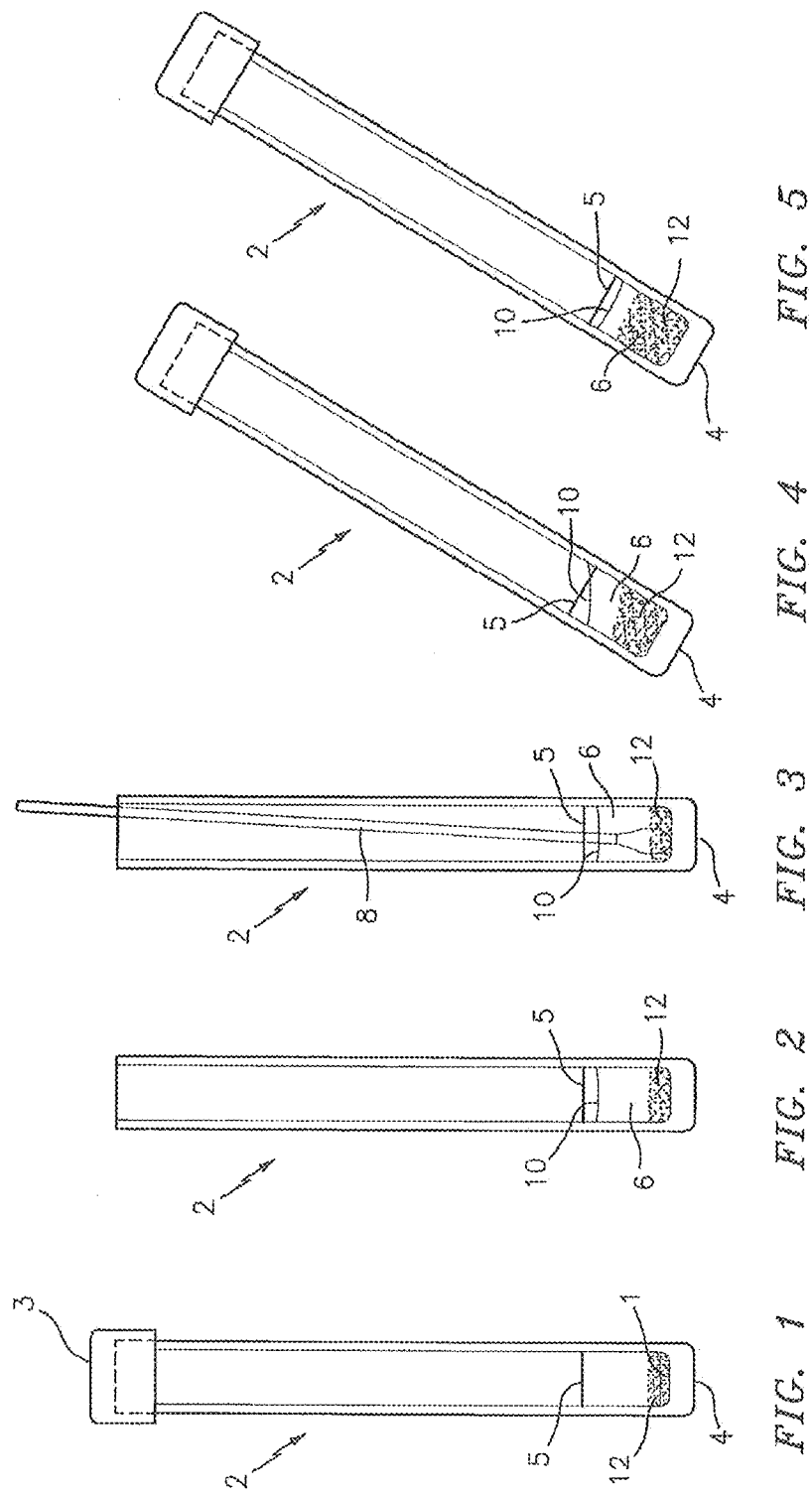

METHOD FOR DETECTING THE PRESENCE OR ABSENCE OF A TARGET MICROBE IN A TEST SAMPLE

This application is a divisional of U.S. patent application Ser. No. 13/943,400 filed Jul. 16, 2013 now U.S. Pat. No. 8,846,336 which is a continuation-in-part of U.S. patent application Ser. No. 12/823,665 now U.S. Pat. No. 8,546,103, which claims the benefit of U.S. Provisional Patent Application Ser. No. 61/269,588 filed Jun. 27, 2009.

BACKGROUND OF THE INVENTION

1. Technical Information

The present method and test mixture relates to the detection of target microbes in a biological, environmental, or food sample, and to those methods and test mixtures capable of detecting the presence of such target microbes in a reduced period of time relative to existing methods and test mixtures. More particularly, aspects of this invention relate to the detection of a target microbe through the use of a not necessarily sterile testing medium that contains a nutrient or nutrients that can be significantly metabolized only by the target microbe and which, once metabolized, alters a characteristic of the sample. The medium is thus a "specific medium" in that it will support significant growth of only the target microbes rather than a general medium that will also support significant multiplication of microbes other than the target microbe to the production of a sensible signal.

2. Background Information

Culture methods for determining the presence or absence of a microbial pathogen or contaminant in a biological, environmental, or food sample typically required multiple steps and take considerable amounts of time before a definitive result could be produced. In addition, it was also necessary to have a skilled technologist practice the method. Nucleic acid detection methods are faster but considerably more expensive than culture methods and require special costly equipment. They are destructive to the target microbe in that it is rendered non-viable and thus inhibits the ability of the laboratory to conduct complete investigations regarding causality. In view of the great potential harm associated with some microbial pathogens and contaminants, it would be desirable to provide a test method and mixture that provides presence or absence of specific results in less time than is typically possible with currently available tests, and one that provides desirable sensitivity.

SUMMARY OF THE INVENTION

Aspects of the present invention relate to a method and test mixture for the specific detection target microbes in a biological, environmental, or food specimen in liquid broth. In particular the invention utilizes micro particles to enhance the ability of the target microbes to develop, metabolize, and/or multiply. This enhancement may result in an increased sensitivity of the analysis, a decreased time of the analysis, or both.

The micro particles increase the surface area in the liquid broth and allow microbes that multiply in vitro to establish a biofilm. In effect, the micro particles act in an analogous way as a catalyst does in a chemical reaction. In the microbiology area, the micro particles provide multiple attachment surfaces for the microbes to "establish residence". Microbes prefer surfaces on which to grow and multiply rather than being free is a liquid environment. For example, the microbes may experience quorum sensing, which accelerates the generation of a biofilm. The biofilm is produced when the microbes multiply, and it yields colonies of microbes that are held together by external capsules, pili, and glycocalyxes of the microbes which, in the broad context, are surface components, such as polysaccharides, proteins and/or mixtures thereof. The micro particles are static, in that they are not consumed but serve as a physical structure that provides shelter and attachment and promotes the multiplication and expression of the target microbe. There may be attached nutritive elements on the micro particles that serve to stimulate the development of the bacterial nidus. The micro particles may be colloidal, in suspension, or a combination. Any materials or structures that encourage the growth of microbes on a biofilm are highly preferred for use in this invention.

While micro particles are a preferred embodiment of the aspects described above, any structure such as a rod or fibers, which increases the surface area inside of the sampling vessel so as to stimulate and accelerate the formation of microbial biofilms that will hasten the growth of the target microbes can be used.

In most applications of the above described aspects of the present invention, it will be desirable to utilize a test mixture that includes the following: a) an effective amount of amino acids; b) an effective amount of nitrogen sources; c) an effective amount of salts; d) an effective amount of vitamins; e) an effective amount of calcium; f) an effective amount of a primary energy source, g) an effective amount of non-target microbe inhibitors, and h) a minimal mass of micro particles. Those skilled in the art will recognize that natural sources of such amino acids can be used rather than pure sources. The natural sources (e.g. extract of whole organisms, such as yeast) may be in mixture form or in purified form. The natural mixtures can contain varying amounts of such amino acids and vitamins. Those skilled in the art will further recognize that many different combinations of amino acids and vitamins can be used in present invention test mixtures.

Those in the art will further recognize that carbon, nitrogen, trace elements, vitamins, amino acids and selective agents can be provided in many forms. Generally, it is preferred to have an amount of vitamins and amino acids within a predetermined range, but those in the art will recognize that the actual properties of each ingredient may be varied so that reduction in the amount of one ingredient can be compensated by an increase in the amount of another. This is particularly relevant when the essential amino acids, trace elements or vitamins of the microbes sought to be detected are known. Some ingredients may be provided in reduced amounts or deleted if they may be synthesized endogenously by the microorganism whose presence is to be determined. Salts may be provided as a source of ions upon dissociation.

The test mixture may be packaged in a container (e.g., a test tube, a container with a flat bottom wall, etc.) that facilitates the testing process. If the medium is prepared in a form that can be hydrated, the mixture can be hydrated with sterile water or non-sterile water.

For example, to detect the presence of MSSA or MRSA within a sample, the sample is obtained from a biological, environmental, or food specimen. A sample collected using a nasal swab is an example of a first generation sample that is particularly convenient to collect and test using the present invention. Once collected, the sample is inoculated into the test mixture. The inoculated sample is incubated under conditions favorable to facilitate the multiplication of any *S. aureus* that may be present within the inoculated sample. In the case of a powdered test mixture hydrated with water, the incubation may be carried out at temperatures between about 20° C. to 42° C. The combination of sequential enzyme specificity, *S. aureus* enhancing growth factors, and antibiotic selectivity provides multiple hurdles which prevent the competing non-target bacteria from being detected within the test period; e.g. 24 hours or less.

The above described aspects of the present invention can be used in hospital admissions, routinely in intensive care units, in nursing homes, dialysis patients, people receiving home immunosuppressive therapy, patients before surgical procedures, and the like. For example, they can also be used in environmental settings (e.g., gyms, tanning salons, restaurants, etc.) whereby the bacteria *S. aureus* may be transferred from a human carrier and it can be used to test various different foods for *S. aureus* contamination. It will be appreciated that a substantial benefit of the aforesaid aspects is that they may be performed/used without the need for expensive equipment or skilled medical technologists. Another substantial benefit of these aspects is that they are operable with a relatively small amount of *S. aureus* within the test sample; e.g., the present method/mixture has detected *S. aureus* in samples having concentrations of *S. aureus* as low as 20 CFU/ml.

According to an aspect of the present invention, a target microbe-specific test mixture for detecting the presence or absence of a target microbe in an environmental or biological sample is provided. The test mixture includes micro particles, a metabolizable substrate, and an amount of vitamin, amino acid, element and salt ingredients. The micro particles are in an amount that is effective to accelerate the formation of microbial biofilms in an admixture of the test mixture and the sample. The metabolizable substrate may be a sugar, sugar alcohol, polysaccharide, amino acid, nutrient-indicator, or peptide that is in an amount that is sufficient to support log phase growth of the target microbe until a detectable characteristic signal is produced in the test mixture and sample admixture. The metabolizable substrate is adapted to directly or indirectly produce the detectable characteristic signal when metabolized by the target microbe. The amount of vitamin, amino acid, element and salt ingredients together allow viability of the target microbe in the presence of the metabolizable substrate and aid the target microbe through lag phase and into log phase reproduction of the target microbe in the sample. The test mixture does not support continued logarithmic growth of any viable non-target microbes in the admixture to any extent where a non-target microbe would impair the detection of the presence of absence of the target microbe.

According to another aspect of the present invention, a specific test mixture for combination with a test sample to determine the presence of absence of a target microbe in the test sample, and which can detect the presence of the target microbe, is provided. The test mixture includes micro particles, operative amounts of essential vitamins and elements needed to support growth of the target microbe, and a metabolizable substrate. The micro particles are in an amount that is effective to accelerate the formation of microbial biofilms in an admixture of the test mixture and the sample. The microparticles are static, in that they serve as a nidus for the multiplication of the target microbe but do not contribute substantially to the nutrient mix. They may have small amounts of nutrients affixed to their structures that facilitate the generation of the nidus and biofilm. The metabolizable substrate is the primary nutrient in the test mixture and is substantially the only nutrient in the test mixture which can be metabolized by the target microbe to the extent needed to support continued reproductive growth thereof to the production of a sensible signal. The metabolizable substrate cannot be substantially metabolized by other viable microbes in the specimen.

According to another aspect of the present invention, a method of detecting the presence or absence of a target microbe in a sample is provided. The method includes the steps of: a) providing a test mixture that includes micro particles in an amount that is effective to accelerate the formation of microbial biofilms in an admixture of the test mixture and the sample, a metabolizable substrate in an amount that is sufficient to support log phase growth of the target microbe until a detectable characteristic signal is produced in the test mixture and sample admixture, an amount of vitamin, amino acid, element and salt ingredients, which amount of ingredients is operable to allow viability of the target microbe in the presence of the metabolizable substrate and to aid the target microbe through lag phase and into log phase reproduction of the target microbe in the sample, wherein the test mixture does not support continued logarithmic growth of any viable non-target microbes in the admixture to any extent where a non-target microbe would impair the detection of the presence of absence of the target microbe; b) combining the powdered test mixture and sample to form the admixture, wherein the metabolizable substrate is adapted to alter a detectable characteristic in the admixture when metabolized by the target microbe; and c) detecting the presence or absence of target microbes in the sample based on the presence or absence of the detectable characteristic.

According to another aspect of the present invention, a specific test mixture for combination with a test sample to determine the presence of absence of a target microbe in the test sample, and which can detect the presence of the target microbe, is provided. The test mixture includes micro particles and operative amounts of one of Colilert®, Colilert18®, or Enterolert®. The micro particles are provided in an amount that is effective to accelerate the formation of microbial biofilms in an admixture of the test mixture and the sample.

The present method and advantages associated therewith will become apparent in light of the detailed description of the invention provided below, and as illustrated in the accompanying drawings.

BRIEF DESCRIPTION OF THE DRAWINGS

FIG. 1 is a side view of a test tube containing a powder test mixture which is formulated to detect the presence or absence of *S. aureus* in a first generation biological sample of a nasal swab.

FIG. 2 is a side view of the test tube of FIG. 1, but showing the culturing mixture having been hydrated by water.

FIG. 3 is a side view of the test tube FIG. 2 and showing a cotton swab inserted into the test tube to deposit a first generation biological specimen nasal swab in the medium.

FIG. 4 is a side view of the test tube of FIG. 3 after the specimen has been deposited and cultured in the medium for a period of time and indicating the absence of *S. aureus* in the specimen.

FIG. 5 is a side view similar to FIG. 4 but showing the test tube medium after the culturing period and indicating the presence of *S. aureus* in the specimen.

DETAILED DESCRIPTION

Figure 6:
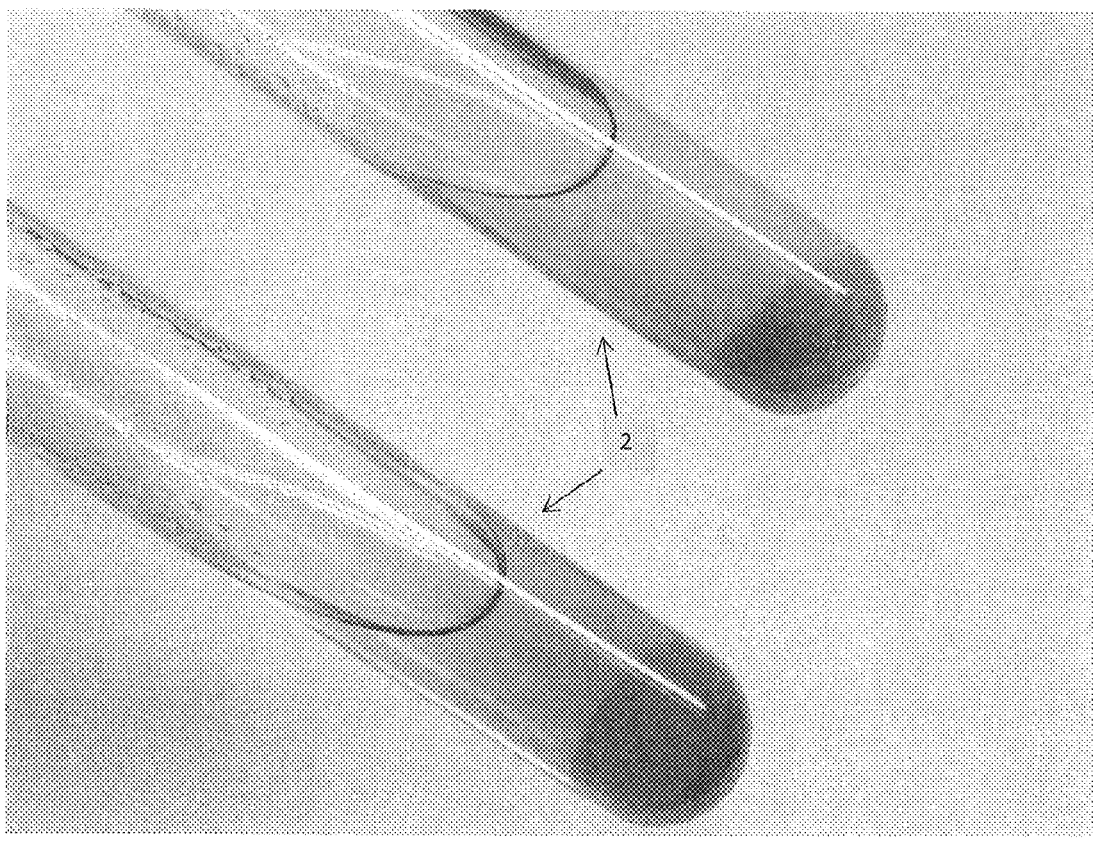
FIG. 6 is an image of an admixture of a water sample and a test mixture including micro particles indicating the presence of targeted microbes within the water sample.

FIG. 1 is a side elevational view of a test tube denoted by the numeral 2 which preferably has a flat bottom 4 and a top closure 3, and which contains a dry powdered test mixture 1 which is formed in accordance with this invention for detecting the presence or absence of S. aureus in a sample; e.g., a first generational biological sample. The tube 2 is also provided with a reference line 5 that indicates the amount of water to be added to the tube 2 in order to properly hydrate the powdered mixture 1 for specimen sample testing. The drawings show the micro particles referred to above as numeral 12 in the sampling tube.

Acceptable hydrated test mixtures can be made using the following constituents in the ranges indicated, to create 15 ml of test mixture:

| Constituent | Quantity per 15 ml of Test Mixture | Range per 15 ml of Test Mixture |
| --- | --- | --- |
| Nitrate Broth | 7.5 ml | 1.0 ml-9.0 ml |
| Water | 7.5 ml | 1.0 ml-9.0 ml |
| Uracil | 10.0 mg | 1.0 mg-20.0 mg |
| Sodium Pyruvate | 10.0 mg | 1.0 mg-20.0 mg |
| L-glutamine | 20.0 mg | 5.0 mg-40.0 mg |
| Sodium Sulfite | 1.0 mg | 0.5 mg-2.0 mg |
| Rabbit Plasma | 100.0 mg | 15.0 mg-500.0 mg |
| Fibrinogen | 100.0 mg | 15.0 mg-500.0 mg |
| Micro Particles | 250.0 mg | 10.0 mg-1000.0 mg |

The specific example of the constituent quantities per 15 ml of test mixture provided above represents a particular test mixture formulation that was tested and found to perform satisfactorily. This specific example does not represent all test mixture formulations, and the present invention is not limited thereto. As stated above, those in the art will recognize that many different combinations of constituents, and varying relative amounts of the same, can be used to provide the same functionality. Hence, the present methods and mixture contemplates that a number of different constituent formulations can be made within the aforesaid ranges.

As indicated above, the addition of micro particles having a size in the range of about 0.1 micron to about 5.0 mm to a present invention test mixture provides localities where bacteria can agglomerate, thereby significantly decreasing the time required for a detectable signal (e.g., a clot or coalescence), and significantly increasing the sensitivity of the test. In those tests where the detectable signal is a clot or coalescence, the micro particles also increase the strength of the clot or coalescence. Acceptable micro particles materials include particles that are "static" with respect to the test at hand; e.g., particles made of glass, phycolloid, agarose, plastic, gelatin, or other similar material.

As noted in FIG. 2, the powdered mixture 1 is properly hydrated by the addition of water, preferably distilled water, to form a hydrated test mixture 6 into which the sample (e.g., carried on a nasal swab) is deposited.

A modification of the above description by the inclusion of an antibiotic allows for the direct detection of antibiotic resistant pathogenic Staphylococcus. For example, the addition of a mecA gene inducer such as cefoxitin or oxacillin can render the example capable of the isolation and detection of the class of antibiotic resistant bacteria known as methicillin resistant staphylococcus aureus. In another modification to the above described example, the addition of vancomycin can allow the direct isolation and detection of either a class of antibiotic resistant staphylococcus know as vancomycin intermediate staphylococcus aureus (VISA) or vancomycin resistant staphylococcus aureus.

Furtheiuiore the addition of a primary specific energy source particular for S. aureus, such as mannitol, can allow for the detection in all the above examples via a color change in the liquid when coupled with a signal generator, such as phenol red.

An experiment was undertaken to determine the sensitivity of an MRSA test mixture formula. Two standard bacteria were utilized. They were a methicillin susceptible Staphylococcus aureus, MSSA, called ATCC 25923 and methicillin resistant Staphylococcus aureus, MRSA, called ATCC 43300. These are two clones of bacteria universally utilized as standards in the field of antibiotic susceptibility testing. The bacteria prepared in concentrations from 9 log 10 to 0 log 10 in final densities MRSA formula and incubated at thirty-five degrees Celsius (35° C.). After a standard incubation period of 18 hours, the MSSA ATCC 25923 showed no production of signal and the MRSA ATCC 43300 showed the generation of a visible signal at 20 bacteria, or colony forming units (cfu). Without the microparticles the limit of detection was 800 CFU First generational test samples can be collected by a variety of different techniques; e.g., a human sample can be collected by wiping a swab within the nose of a subject. Nasal swabs are a particularly convenient way of collecting a test sample, but they are not the only collection method; e.g., test samples can be collected from throat swabs, skin lesions, undamaged skin, etc. First generational environmental samples can be collected by various known methods; e.g., wiping or swabbing a surface using a dry or wet wipe/swab. Likewise, first generational food samples can be collected form the food itself, or wiping food residue from surfaces in contact with the food, etc. Once the sample is collected, it can be deposited in the hydrated test mixture 6; e.g., using the same cotton swab 8 which has been used to gather the first generation sample from the source thereof. Once the specimen sample is deposited in the test mixture 6, it is incubated within the test mixture for a period of time typically less than twenty-four hours. The incubation may occur at any temperature that is acceptable under the circumstances. After the inoculation period, the container (e.g., test tube 2) holding the inoculated test mixture can be inspected for the presence of a clot; e.g., the test tube 2 can be tilted to one side as shown in FIGS. 4 and 5 to see if the meniscus 10 of the test mixture will move or whether a clot keeps the test mixture below a reference line 5. The presence of a clot indicates that S. aureus is present in the test sample, and the absence of a clot in the inoculated test mixture indicates that S. aureus is not present in the test mixture 6, as shown in FIG. 4. In some instances, the entire inoculated test mixture will clot, and in others some liquid will remain in the container with the clot. Approximately 80% of the present tests performed using first generation nasal samples clotted within six hours when S. aureus is present in the first generation test sample.

To determine the effectiveness of aspects of the present method and mixture, a control study was performed involving sixty (60) control samples titrated to contain varying amounts of MSSA, and sixty (60) control samples containing varying amounts of MRSA. Standard clones of MSSA and MRSA were grown in trypticase soy broth (TSB), and were diluted by log 10 increments. The present invention test mixture was inoculated with a set amount (0.1 ml) of each the control samples. A first set of the inoculated test mixtures were incubated at 35° C., and second set of the inoculated test mixtures were incubated at 23° C. Of the sixty control test samples, all were positive for S. aureus in five hours, forty-nine (49) were positive in four hours; thirty-six (36) were positive in three hours, and twenty-four (24) in two hours. Data detailing the relationship between the concentration of the inoculum, and incubation temperature was as follows:

| S. aureus CFU/ml | Clot at 35° C. without particles | Clot at 35° C. with particles |
| --- | --- | --- |
| 7 log 10 | 2.0 hr | 1.5 hr |
| 6 log 10 | 3.0 hr | 2.25 hr |
| 5 log 10 | 4.0 hr | 3.0 hr |
| 4 log 10 | 6.0 hr | 4.5 hr |
| 3 log 10 | 10.0 hr | 8.0 hr |
| 2 log 10 | 15.0 hr | 12.0 hr |

In some embodiments, the present method/mixture may include means to distinguish between MSSA and MRSA. For example, cefoxitin in a concentration of about 2-10 mcg/ml or another MecA gene inducer can be included in the test mixture. Any MSSA present within the test sample will be killed, but MRSA will not. Thus, if a clot does form, the S. aureus in the test sample will have been shown to be MRSA. If a clot forms and confirms the presence of MRSA, the clot can then be dissolved in order to perform further analyses of the S. aureus bacterium detected. In some embodiments, a metabolizable substrate or substrates (e.g., a metabolizable substrate) may be included to enhance the specificity of the test. These may include a hydrolyzable substrate, sugar, or amino acids. When metabolized by the target microbe, a sensible signal is produced that provides an additional indication that the target microbe is present, thus enhancing specificity.

It will be appreciated that test aspects of this invention are significantly simpler to perform than the standard tests which are currently in use, as typified by the coagulase plasma procedure suggested by Remel Products, Thermo Fisher Scientific, Lenexa, Kans., U.S.A. The Remel procedure, which is approved by the FDA and appears in the Code of the Federal Register as an exempt test, requires a two-step test for S. aureus wherein microbe colonies from the specimen are first grown in an agar medium and screened for suspected S. aureus colonies using a gram stain and catalase slide test before proceeding to a second coagulase test step. There are complications relating to the Remel type of coagulase test, namely: 1) colonies for coagulase testing must not be picked from media containing high concentrations of salt as false positive results may occur; 2) in the first step slide test procedure, the organism/saline suspension must be observed for auto-agglutination prior to the addition of the coagulase plasma to prevent a false positive test reading; and 3) false negative coagulase reactions may occur if the test culture is older that 18-24 hours, or if there is scant growth.

Additional aspects of the present invention detect target microbes in a sample by using a test mixture with a metabolizable substrate which is the preferred or primary nutrient for the target microbe but cannot be substantially metabolized by any other viable microbes which may be present in the sample along with the target microbe. The detection sensitivity and speed at which detection can occur is enhanced by the addition of micro particles to the test mixture. In some embodiments, the metabolizable substrate will directly or indirectly change a characteristic of a test sample/test mixture admixture once the metabolizable substrate is metabolized by the target microbe. The characteristic can be: color (either visible, ultra violet, or infrared); electrical conductivity; electrical impedance; or the like. The preferred mode of performing these aspects involves detecting the target microbes by use of a metabolizable substrate in the test mixture which, when metabolized, changes the visible or fluorescent color of an aqueous solution containing the specimen.

The metabolizable substrate actively participates in the growth of the target microbes by serving as the preferred or primary nutrient source for an essential element required for growth, such as energy or nitrogen. The target microbes can grow, metabolize, and multiply because they, and substantially only they, can use the metabolizable substrate as their primary nutrient. Metabolizable substrates can include chromogens attached to: salts; carbon; nitrogen; sulfur; amino acids; fatty acids; peptides; or other selective primary nutrients for microbes. Because microbes other than the target microbes are inhibited from growing, metabolizing, or multiplying, the test mixture is so specific that it does not have to be sterilized before use. Competition between target microbes and other microbes in the sample for the available nutrients in the test mixture is eliminated. The test mixture can be manufactured and packaged in a powder form that is added to the sample being tested. The test mixture can be dissolved in water and the sample can be added to the solution, or, if the sample is aqueous, the test mixture can be directly admixed with the sample. There is no need for a minimum incubation time to ensure growth of the target microbe in the admixture since no other microbes in the sample will be able to substantially metabolize the nutrient in the test mixture.

In some embodiments, the test mixture may also include a minor amount of a growth accelerant that will boost the target microbes and all of the other viable microbes in the sample through lag phase toward log phase of growth in the testing procedure. It will be understood by those skilled in the art that when a sample, such as environmental samples, are tested in accordance with the procedure of this invention, is combined with a test mixture according to the present invention, all of the microbes in the sample will lapse into a lag phase of growth, due to the newness of the environment they are in. In the lag phase, none of the microbes will significantly multiply and grow until they adjust to the new environment. This dormant stage, (which all of the microbes, including the targets encounter) can increase the test period. The growth accelerant which can be incorporated into the test mixture is a combination of natural plant extracts, vitamins, and minerals which hasten the transition of the target microbes, and all of the other microbes in the sample, through the lag phase and into the log phase so as to lessen the time duration from the inception of the test to the alteration (or no alteration) of the sample which indicates the presence (or absence) of the target microbes in the sample. The total time lapse will be reduced by about one half by inclusion of the accelerant in the medium. The accelerant is present in a small amount so as to be dissipated by the time the microbes enter log phase of growth.

The development of a specific color can indicate the presence of the target microbes. This may occur at any time after the procedure is initiated. There is no need to purify the target microbes. There is no need to perform any chemical analysis of the sample to determine whether the target microbe is present.

As used herein, the term "target microbes" can refer to a single microbe, a related species of microbes, or a large genus of microbes possessing a common taxonomic characteristic. The metabolizable substrate only needs to be specific to the "target microbe." For example, metabolizable substrates are available for detecting a single microbe, such as *Escherichia coli* (*E. coli*), or for detecting any one of a closely related species of microbes, such as *Klebsiella—Enterobacter—Serratia,* or any one of a large genus of microbes, such as Gram negative bacteria. In those embodiments where the metabolizable substrate includes a chromogen, the metabolizable substrate can produce color in the visible range, the ultraviolet range, or the infrared range. As will be appreciated from the aforesaid, the metabolizable substrate may be colorless in the non-metabolized state, and will preferably release a color moiety after being metabolized by the microbes. The color may be visible, fluorescent, or machine-readable, or some combination thereof As previously noted, using the test mixture according to these aspects of the present invention, there is very little or no competition the metabolizable substrate among the microbes in the admixed test mixture because it is the only metabolizable substrate present in the admixed test mixture can be metabolized to any significant extent solely by the target microbes. Accordingly, a significant number of false-negative tests which may occur with the procedures of the prior art are eliminated using the present test mixture. The nutrient used will be one that the target microbes greatly prefer over any other nutrients, and also, one to which other microbes have little or no preference. Thus, only the presence of the target microbes in the specimen can result in sufficient metabolism of the nutrient to cause the color or other characteristic change in the admixed test mixture.

*Escherichia Coli*

A metabolizable substrate that can be used to detect the presence *Escherichia coli* (*E. coli*) is a substrate for the enzyme B-glucuronidase. If one wishes to determine the presence of *E. coli* by a color change, examples of a metabolizable substrate that may be used include orthonitrophenyl-B-D-glucuronide (yellow), B-napthalamide-B-D-glucuronide (purple), alpha-napthol-B-D-glucuronide (red), or methylumbilliferyl-B-D-glucuronide (fluorescent), chlorophenol-red-B-D-galactopyranoside (magenta), or the like. The metabolizable substrate serves as the essential source of carbon. The rest of the test mixture is tailored so that each ingredient provides a requirement for *E. coli*. To prevent competition from microbes other than the broad category of gram negative bacteria, antibiotics such as vancomycin and/or ansiomycin may be added in the percent by weight of 5%. These antibiotics may be present in the range of 0.0001 grams to 0.5 grams per liter To select *E. coli* bacteria, a test mixture including the following ingredients may be used:

| Ingredient | Source | Preferred % by weight | Range % by weight |
|---|---|---|---|
| Nitrogen | ammonium sulfate | 37.0 | 10-50 |
| Amino Acids | Histidine | .0697 | 0.02-0.1 |
| | methionine | .1860 | 0.02-0.4 |
| | tryptophan | .2325 | 0.02-0.5 |
| Vitamins | Biotin | .000232 | 0.0001-0.001 |
| | pantothenate | .0093 | 0.001-0.03 |
| | folic acid | .000232 | 0.001-0.02 |
| | inositol | .0186 | 0.01-0.02 |
| | p-aminobenzoic acid | .046 | 0.01-0.1 |
| | pyridoxine hydrochloride | .093 | 0.05-0.3 |
| | riboflavin | .037 | 0.01-0.06 |
| | thiamine | .037 | 0.01-0.06 |
| Elements | ferric chloride | .046 | 0.02-0.1 |
| | copper sulfate | .001860 | 0.001-0.002 |
| | manganese sulfate | .0037 | 0.002-0.007 |
| | potassium chloride | .0000009 | 0.00001-0.001 |
| | potassium iodide | .0000046 | 0.000001-0.00001 |
| | zinc sulfate | .046 | 0.01-0.08 |
| | boric acid | .460 | 0.01-0.5 |
| | magnesium chloride | .019 | 0.01-0.05 |

-continued

| Ingredient | Source | Preferred % by weight | Range % by weight |
|---|---|---|---|
| Salts | potassium phosphate monobasic | 9.0 | 1-15 |
| | potassium phosphate dibasic | 23.0 | 2-30 |
| | sodium carbonate | 23.0 | 2-30 |
| | magnesium sulfate | 4.6 | 1-10 |
| | sodium chloride | .9 | 0.2-5 |
| | calcium chloride | .9 | 0.2-5 |
| | sodium pyruvate | .023 | 0.01-0.1 |
| Metabolizable Substrate | | .345 | 0.02-2 |
| Micro Particles | Glass, Plastic, Phycocolloid, Zirconium, Silica gel | 3 grams/100 mL | 0.1-10 grams/100 mL |

The metabolizable substrate could include a number of glucuronide hydrolysable substrates such as MUG.

The aforesaid test mixture with a nutrient indicator one skilled in the art would select, such as ONP-B-D-galactopyranoside or CRP-B-D-galactopyranoside, is specific for the total coliform group of bacteria.

The aforesaid test mixture with a nutrient indicator one skilled in the art would select, such as ONP-B-D-galactopyranoside or CRP-B-D-galactopyranoside or others, is specific for the total coliform group of bacteria and, with a second nutrient indicator one skilled in the art would chose, such as MUG or others, would be specific for the simultaneous detection of *E. coli*.

The aforesaid test mixture is an example of an acceptable test mixture, and aspects of the present test mixture are not limited to these examples.

As indicated above, the micro particles are understood to increase the surface area in the sample/test mixture admixture and allow microbes that multiply in vitro to establish a biofilm The micro particles provide multiple attachment surfaces for the microbes to "establish residence". Microbes prefer surfaces to grow and multiply on a surface rather than while being free in a liquid environment. The microbes experience quorum sensing, which accelerates the generation of a biofilm. The biofilm is produced when the microbes multiply, and it yields colonies of microbes that are held together by external capsules of the microbes which, in the broad context, are surface components, such as polysaccharides, proteins and/or mixtures thereof. The micro particles may be colloidal, in suspension, or not in suspension. As indicated above, the micro particles can be made of glass, phycocolloid, agar, agarose, plastic, zirconium, silica gel, gelatin, or any material that is static within the sample/test mixture admixture; i.e., the micro particles do not negatively affect the results of the test. Micro particles (e.g., uncoated glass beads) with a diameter in the range of about 0.01-5.0 mm are useful, and testing to date indicates that micro particles with a diameter in the range of about 0.01-1.0 mm work particularly well. Other structures (e.g., rods) that increase the surface area inside of the sampling vessel so as to stimulate and accelerate the formation of microbial biofilms that will hasten the growth of the target microbes may be used alternatively.

Examples of metabolizable substrates that can be used with aspects of the present invention are provided below.

*Enterococcus*

The *Enterococcus* group, as represented by *Streptococcus faecalis* (*S. faecalis*) and *S. faecium*, is a microbe genus found as a cause of urinary tract infection. It is also the major bacterium analyzed in swimming and recreation water. A metabolizable substrate that can be used to detect the presence of *Enterococcus* is a substrate of the enzyme L-pyronidonyl aminopeptidase. Other substrates include those in the beta-glucosidase family. If one wishes to determine the presence of *Enterococcus* by a color change, examples of ametabolizable substrate that can be used include orthonitrophenyl-B-L-pyronidonyl (yellow), B-napthalamide-B-L-pyronidonyl (purple) (PYR), alpha-napthol-B-L-pyronidonyl (red), and methylumbilliferyl-B-L-pyronidonyl (fluorescent), and esculin (black in the presence of iron salt). The metabolizable substrate serves as the key source of carbon. The remainder of the test mixture may be tailored so that each ingredient provides a requirement for *Enterococcus*. To prevent competition from microbes other than the broad category of gram positive bacteria, antibiotics such as colistin, naladixic acid, or ansiomycin may be added. The metabolizable substrate may be included in a concentration of 0.345 percent by weight of nutrient indicator (the usable range being about 0.02 to about 2.0 percent by weight) or 1 gram per liter of esculin (usable range being about 0.01-10 grams per liter) and the antibiotics may be included in the concentration of 0.005 weight by weight, the usable range being about 0.0001 to about 0.01 weight by weight. The hydrolysis of PYR may be directly detected by the inclusion of a cinnamaldehyde reagent.

A substrate for the enzyme beta-glucosase can also be used. Such substrates include ONP-beta-d-glucopyranoside, 4-methylumbilliferone-beta-d-glucopyranoside, and 6,7-dihydroxycoumarin-b-d-glucose.

Specificity may be enhanced by incorporating both a substrate of the enzyme L-pyronidonyl aminopeptidase and a substrate for the enzyme beta-glucosidase.

A formula that is pre-mixed and compatible with micro particles is Enterolert®, (Idexx, Westbrook, Me.). Without vancomycin, Enterolert® will detect all *Enterococcus*; with 6 mg/liter vancomycin Enterolert® will detect vancomycin resistant *Enterococcus*. U.S. Pat. Nos. 6,355,449 and 7,018,807, each of which is hereby incorporated by reference in its entirety, disclose examples of such test mixtures that can be used with aspects of the present invention.

Pseudomonas Aeruginosa

*Pseudomonas aeruginosa* (*P. aeruginosa*) is a cause of infection in the immunosuppressed, burn patients, and patients with leukemia. It is also an important pathogen in the eye as associate with cosmetics. An example of a text mixture that can be used to detect *P. aeruginosa* directly from a first generation sample includes the following ingredients described in terms of ingredient amount by weight per liter of hydrated test mixture:

| Test Mixture Ingredient | Amount by weight per liter of hydrated test mixture | Range by weight per liter of hydrated test mixture |
| --- | --- | --- |
| Enzymatic Digest of Gelatin | 20 gms | 2-40 gms |
| Magnesium Chloride | 1.4 gms | 0.1-5 gms |
| Potassssium Chloride | 10 gms | 1-20 gms |
| Cetrimide (Cetyltrimethylammonium Bromide) | 0.3 gms | 0.1-1 gms |
| Phycocolloid | 9 grams | 0.5-20 gms |
| Gelatin | 1.0 gms | 0.01-5 gms |
| Calcium Carbonate | 1.0 gms | 0.01-2 gms |

Specificity for *Pseudomonas aeruginosa* of the mixture can be enhanced by the incorporation of a phenylacridan variant in the amount of 3 mg per liter (from 0.1-40).

The above test mixture example is hydrated and adjusted as required to have a pH of about 7.2. When the above described example of a hydrated test mixture is inoculated with a test sample (e.g., a first generation sample) containing a detectable amount of *P. aeruginosa*, the hydrated test mixture will contain detectable fluorescent molecules and blue/green pigmentation produced by the *P. aeruginosa* metabolizing a metabolizable substrate (e.g., enzymatic digest of gelatin) within the test mixture.

Klebsiellae

A primary carbon source may be used as the primary nutrient in the detection of the total coliform group in water. In addition, when a carbapenem type antibiotic is included in the formula, the detection of resistant total coliforms and related bacteria (called KPC, *Klebsiella* Producing Carbapenamase or CRE, Carbapenamase Resistant *Enterobacteriaceae*) can be detected. The bacteria in the family Klebsiellae can metabolize carbon sources in which carbon in sugar molecules are attached by B-D linkages. A test mixture directed toward this species includes a metabolizable substrate having a primary carbon nutrient source, a glucose molecule attached through the B-D linkage to orthonitrophenyl, a chromogenic moiety, and the antibiotics colistin and naladixic acid. If the total coliform group is present in a sample admixed with the test mixture, the orthonitrophenyl-B-D-glucose will be metabolized with the release of the orthonitrophenyl moiety. This moiety, when released, becomes yellow. Therefore, the yellow color in the admixture indicates the presence of the target microbes, i.e., the total coliforms. Other microbes will not grow because they cannot metabolize the metabolizable substrate, orthonitrophenyl-B-D-glucose. Alternatively, the metabolizable substrate CPRG (chlorophenyl red B-D-galactopyranoside) may substitute for the orthonitrophenyl. There will not be microbial competition with other microbes, because they will not grow and metabolize to produce a sensible signal.

An example of a CRE medium in which particles accelerate the growth of the target microbes include:

| Ingredient | Source | Preferred % by weight | Range % by weight |
| --- | --- | --- | --- |
| Nitrogen | ammonium sulfate | 37.0 | 10-50 |
| Amino Acids | Histidine | .0697 | 0.02-0.1 |
| | methionine | .1860 | 0.02-0.4 |
| | tryptophan | .2325 | 0.02-0.5 |
| Vitamins | Biotin | .000232 | 0.0001-0.001 |
| | pantothenate | .0093 | 0.001-0.03 |
| | folic acid | .000232 | 0.001-0.02 |
| | inositol | .0186 | 0.01-0.02 |
| | p-aminobenzoic acid | .046 | 0.01-0.1 |
| | pyridoxine hydrochloride | .093 | 0.05-0.3 |
| | riboflavin | .037 | 0.01-0.06 |
| | thiamine | .037 | 0.01-0.06 |
| Elements | ferric chloride | .046 | 0.02-0.1 |
| | copper sulfate | .001860 | 0.001-0.002 |
| | manganese sulfate | .0037 | 0.002-0.007 |
| | potassium chloride | .0000009 | 0.00001-0.001 |
| | potassium iodide | .0000046 | 0.000001-0.00001 |
| | zinc sulfate | .046 | 0.01-0.08 |
| | boric acid | .460 | 0.01-0.5 |
| | magnesium chloride | .019 | 0.01-0.05 |

-continued

| Ingredient | Source | Preferred % by weight | Range % by weight |
|---|---|---|---|
| Salts | potassium phosphate monobasic | 9.0 | 1-15 |
| | potassium phosphate dibasic | 23.0 | 2-30 |
| | sodium carbonate | 23.0 | 2-30 |
| | magnesium sulfate | 4.6 | 1-10 |
| | sodium chloride | .9 | 0.2-5 |
| | calcium chloride | .9 | 0.2-5 |
| | sodium pyruvate | .023 | 0.01-0.1 |
| Metabolizable Substrate | | .345 | 0.02-2 |
| Micro Particles | Phycocolloid | 3 gms/100 mL | 0.1-10 gms/100 mL |
| Antibiotics | Meropenem | 2 milligrams/L | 0.25-20 milligrams/L |
| | Ciprofloxacin | 2 milligrams/L | 0.5 to 4 milligrams/L |

A representation of a pre-mixed formula in the above example, less the micro particles, include Colilert®, Colilert-18®, and Colisure® (Idexx, Westbrook, Me.).

Tests were conducted to evaluate the effects of using micro particles with several different test mixtures for the detection of a bacterium representative of CRE, an *E. coli*. Referring to FIG. 6, an image of a pair of test tubes 2 is shown. The test tubes 2 include a water sample inoculated with *E. coli*, and admixed with a test mixture including metabolizable substrate designed to detect the presence of *E. coli* within the water sample via color change, and micro particles. The hydrated test mixture has an initial straw colored appearance. The color of the admixture changes to purple to indicate the presence of *E. coli*. As can be seen in the images, the color purple is predominantly found in the bottom of the test tubes 2. The concentration of the color purple (indicating the presence of *E. coli*) at the bottom of the test tubes reflects the higher concentration of *E. coli* microbes in the admixture residing in the bottom of the test tubes, where particles have gravitationally settled and microbial biofilms have developed, attached to the particles. Additional particles are distributed with the remainder of the admixture, but have not yet been associated with metabolizable substrate creating a color change. The image of the test tubes illustrates well how the particles expedite the detection of the bacteria (i.e., *E. coli*) targeted by the metabolizable substrate of the test mixture, and the increased sensitivity associated therewith; i.e., the micro particles provide surface area/attachment surfaces for the *E. coli* microbes to establish residence, grow, and multiply (e.g., creating biofilms), which growth is indicated by the color change created when the nutrient portions of the metabolizable substrate are metabolized by the microbes.

In another test, two identical test mixtures including nutrient indicators were prepared to determine the presence or absence of the bacteria *Klebsiella* in water samples. A water sample was inoculated with quality control clones of the bacterium *Klebsiella* produced by Idexx Laboratories, Inc. In each test, seven levels of sample dilution were prepared (no dilution; $1:10^1$; $1:10^2$; $1:10^3$; $1:10^4$; $1:10^5$; and $1:10^6$). A predetermined amount of the test mixture without micro particles was added to each of the seven test tubes in a first set (same amount of test mixture in each test tube). The same predetermined amount of the test mixture was added to a second set of seven test tubes. In this instance, however, micro particles were added to each of the predetermined test mixture amounts. The diluted samples were added to the each set of test tubes. In the *Klebsiella* test using the test mixture without micro particles, over an observation period of 16 hours with the sample/test mixture admixture maintained at thirty-five degrees Centigrade (35° C.), each dilution indicated (by a color change) the presence of the bacteria *Klebsiella*, with the exception of the largest dilution ($1:10^6$) which did not indicate a color change. In the *Klebsiella* test using the test mixture with micro particles, over an observation period of 16 hours with the sample/test mixture admixture maintained at thirty-five degrees Centigrade (35° C.), every dilution indicated (by a color change) the presence of the bacteria *Klebsiella*. Consequently, the test mixture including the micro particles was found to be about ten times (10×) more sensitive than the test mixture without the micro particles. Tests performed using Colilert® and Colilert 18 ® (Idexx Laboratories Inc., Westbrook, Me., USA), both of which utilize a nutrient-indicator as a primary food source, showed a major decrease in the time required to results (e.g., on the order of 3-5 hours at 10 bacteria per mL) when the particles were present. This decrease in time is very significant in the field of water analysis, whereby the public health is being protected.

In a third test, two identical test mixtures including metabolizable substrates (which test mixtures were different from those used in the first test) were prepared to determine the presence or absence of the bacteria *Klebsiella* in water samples. The second test used the same test procedures used in the first test, which procedures are described above. Phycocolloid powder was used as the micro particles in the second test. In this second test, the second test mixture with micro particles was found to be about one hundred times (100×) more sensitive than the second test mixture without the micro particles.

In each test, uninoculated samples were tested using both test mixture without micro particles and test mixture with micro particles as negative controls. No false positives were indicated.

A number of other tests were performed using the commercially available Colilert® and Colilert-18® water test products offered by Idexx Laboratories, Inc., mixed with different micro particles (e.g., phycocolloids, Accumedia™ agar, Difco™ Bacto agar, zirconium, and silica gel). In these tests, periodic evaluations were performed to determine minimum times required for positive detection of both *Klebsiella* and *E. coli*, separately. While there was variation in the efficacy of each micro particle to decrease the time to detection, the results of these tests indicate positive detection results in as little as one hour, and in most instances positive results were indicated in less than five (5) hours, a decrease in time of 20% to 200%. Here again, negative controls were included in the testing procedures with no false positives indicated. The Colilert® water test product is marketed as being able to produce results in twenty-four (24) hours or less. The Colilert-18® water test product is marketed as being able to produce results in eighteen (18) hours or less. With the particles, the Colilert® produced positive results in 18 hours or less and the Colilert 18 in 14 hours or less.

One experiment was conducted to determine the effects of particles on the ability of Colilert 18® to detect very small concentrations of *E. coli*. A test mixture was made including *E. coli* at a concentration of 10 bacteria per 100 mL Micro particles were added to a first portion of the test mixture at a concentration of 4 grams per 100 mL, and no micro particles were added to a second portion of the test mixture. It was found that Colilert 18® indicated positive results in the test mixture without the micro particles in 12 hours; however with the test mixture with the micro particles indicated a positive signal in 7 hours.

According to an aspect of the present invention, therefore, the micro particles described herein may be incorporated into the commercially available formulas of Colilert®, Colilert18®, Enterolert®, or variations of any of these products, all of which are marketed by Idexx Laboratories of Westbrook Me., USA. The formulas for these products are believed to be published in the Federal Register; e.g., for Colilert®: p. 24748, Federal Register Vol. 57, No. 112, Jun. 10, 1992, Rules and Regulations.

While the invention has been described with respect to specific embodiments, those skilled in the art will readily appreciate that various changes and/or modifications can be made to the invention.

What is claimed is:

1. A method of detecting the presence or absence of a target microbe in a test sample, said method comprising the steps of:
   providing a test mixture that includes organic micro particles in a form that promotes the formation of a microbial biofilm, operative amounts of essential vitamins and elements needed to support growth of the target microbe, and a metabolizable substrate in the test mixture and which can be metabolized by the target microbe to the extent needed to support continued reproductive growth thereof, and which cannot be metabolized by other viable microbes in the test sample, whereupon a sensible characteristic of the sample is altered when the substrate is metabolized;
   providing a test sample obtained from a biological, environmental, or food source, and combining the test sample in unprocessed form with the test mixture to form an admixture;
   wherein the micro particles are in a relative amount within the test mixture that is effective to accelerate the formation of microbial biofilms within the admixture of the test sample and the test mixture; and
   detecting the presence or absence of target microbes in the sample based on the presence or absence of the detectable characteristic.

2. The method of claim 1 further comprising the step of hydrating the test mixture.

3. The method of claim 1, wherein the micro particles comprise at least one of phycocolloid, gelatin, agar, or agarose.

4. The method of claim 1, wherein the micro particles are agar powder particles.

5. The method of claim 1, wherein the micro particles are agarose powder particles.

6. The method of claim 1, wherein the micro particles are gelatin powder particles.

7. The method of claim 1, wherein the micro particles are phycocolloid powder particles.

8. The method of claim 1, wherein the micro particles have a diameter in the range of about 0.001 mm-5.0 mm.

9. The method of claim 1., wherein the test mixture is specific for detecting the presence or absence of E. coli as the target microbe.

10. The method of claim 1, wherein the test mixture is specific for detecting the presence or absence of total coliforms as the target microbe.

11. The method of claim 1, wherein the test mixture is specific for detecting the presence or absence of carbapenamase producing bacteria as the target microbe.

12. The method of claim 1, wherein the test mixture is specific for detecting the presence or absence of P. aeruginosa as the target microbe.

13. The method of claim 1, wherein the test mixture is specific for detecting the presence or absence of S. aureus as the target microbe.

14. The method of claim 1, wherein the test mixture is specific for detecting the presence or absence of Enterococcus as the target microbe.

15. The method of claim 1, wherein the test mixture is specific for detecting the presence or absence of KPC (Klebsiella Producing Carbapenamase) as the target microbe.

16. The method of claim 1, wherein the test mixture is specific for detecting the presence or absence of CRE (Carbapenarnase resistant enterobacteriaceae) as the target microbe.

17. The method of claim 1, wherein the test mixture is specific for detecting the presence or absence of MRSA (methicillin resistant Staphylococcus aureus) as the target microbe.

18. The method of claim 1, wherein the test mixture is specific for detecting the presence or absence of VISA (vancomycin intermediate Staphylococcus aureus) as the target microbe.

19. The method of claim 1, Wherein the test mixture is specific for detecting the presence or absence of VRSA (vancomycin resistant Staphylococcus aureus) as the target microbe.

20. The method of claim 1, wherein the test mixture includes an effective amount of sat least one inhibitor to a non-target microbe.

21. The method of claim 1, wherein the operative amounts of essential vitamins and elements needed to support growth of the target microbe includes operative amounts of ammonium sulfate, manganese sulfate, zinc sulfate, sodium chloride, calcium chloride, and sodium sulfite.

22. The method of claim 1, wherein the metabolizable substrate includes operative amounts of orthonitrophenyl-B-D-glucuronide and methylumbilliferyl-B-D-glucuronide.

23. The method of claim 1, wherein the metabolizable substrate includes an operative amount of a B-glucuronidase enzyme.

24. The method of claim 1, wherein, the metabolizable substrate includes a glucuronide hydrolysable substrate.

25. The method of claim 1, wherein the metabolizable substrate includes operative amounts of chlorophenol red-β-D-galactopyranoside (CPRG) and methylumbilliferyl-B-D-glucuronide.

* * * * *